US008685436B2

(12) United States Patent
Ley et al.

(10) Patent No.: US 8,685,436 B2
(45) Date of Patent: Apr. 1, 2014

(54) USE OF HYDROXYFLAVANONES FOR MASKING BITTER TASTE (75) Inventors: Jakob Peter Ley, Holzminden (DE); Gerhard Krammer, Holzminden (DE); Günter Kindel, Höxter (DE); Ian-Lucas Gatfield, Höxter (DE); Manfred Müller, Holzminden (DE)

(73) Assignee: Symrise AG, Holzminden (DE)

( * ) Notice: Subject to any disclaimer, the term of this patent is extended or adjusted under 35 U.S.C. 154(b) by 1728 days.

(21) Appl. No.: 10/141,426

(22) Filed: May 8, 2002

(65) Prior Publication Data

US 2002/0188019 A1     Dec. 12, 2002

(30) Foreign Application Priority Data

May 11, 2001    (DE) .................................. 101 22 898

(51) Int. Cl.
     *A61K 47/00*      (2006.01)
     *A61K 9/68*      (2006.01)
     *A23L 1/22*      (2006.01)
     *A61K 31/35*      (2006.01)

(52) U.S. Cl.
     USPC ........... 424/439; 424/440; 424/441; 426/534; 426/536; 426/650; 514/456

(58) Field of Classification Search
     USPC ............................ 424/439, 440; 514/974, 975
     See application file for complete search history.

(56) References Cited

U.S. PATENT DOCUMENTS

| 4,154,862 | A | | 5/1979 | Guadagni et al. ............. 426/536 |
| 4,371,551 | A | * | 2/1983 | Fulger et al. .................... 426/28 |
| 4,567,053 | A | | 1/1986 | Lindley ......................... 426/538 |
| 5,248,501 | A | * | 9/1993 | Parnell .......................... 424/774 |
| 5,560,913 | A | * | 10/1996 | Kupper ........................ 424/732 |
| 5,580,545 | A | | 12/1996 | Washino et al. ................ 424/49 |
| 5,703,053 | A | | 12/1997 | Kurtz et al. ............. A61N 43/16 |
| 5,877,208 | A | * | 3/1999 | Bok et al. ...................... 514/456 |
| 6,083,459 | A | | 7/2000 | Mukai et al. .................... 422/40 |
| 6,565,877 | B1 | * | 5/2003 | Mukherji et al. ............. 424/441 |

FOREIGN PATENT DOCUMENTS

| CN | 1186612 A | * | 7/1998 |
| EP | 774249 A2 | * | 5/1997 |
| EP | 0 635 218 | | 10/2000 |
| JP | 61260862 A | * | 11/1986 |
| JP | 11-100325 | | 4/1999 |
| WO | 00/21390 | | 4/2000 |
| WO | WO 00/23073 | * | 4/2000 |

OTHER PUBLICATIONS

Aviado et al. Drug therapy of acute pulmonary insufficiency. U.S. NTIS, AD-A Rep. No. 007214, p. 57.*

(Continued)

*Primary Examiner* — Lakshmi Channavajjala
(74) *Attorney, Agent, or Firm* — Duane Morris LLP; J. Rodman Steele, Jr.; Gregory M. Lefkowitz (57) ABSTRACT The invention relates to hydroxyflavanones, their salts and stereoisomers and their mixtures for suppressing or reducing the bitter and/or metallic taste impression. In addition, the invention relates to nutritional, nutritive or consumable preparations or oral pharmaceutical compositions, characterized in that these have an active content of hydroxyflavanones, their salts and stereoisomers or their mixtures.

20 Claims, 3 Drawing Sheets

(56) References Cited

OTHER PUBLICATIONS

Aviado-U.S. NTIS, AD-A Rep. 1975. No. 007214, 7s (10), 45. p. 157-165 of NTIS booklet.*

Singh et al. Production and sensory characterization of a bitter peptide production from beta-casein. J. Agric. Food Chem. 2005 Feb 23; 53(4); 1185-9. (abstract only).*

Bocco et al. Antioxidant activity and phenolic composition of citrus peel and seed extracts. Journal of Agricultural and Food Chemistry (1998), 46(6), 2123-2129 (abstract only).*

Karuza et al. Isolation and structure of flavonoids from peppermint (Mentha C piperita) leaves. Acta Pharmaceutica (Zagreb) 1996, 46(4), 315-320 (abtract only).*

Metabolic fate of hesperidin, eriodictyol, homoeridictyol and siosmin. J. Biol. Chem. 1958, 230:pp. 655-660.*

Liu et al. Isolation of potential cancer chemopreventive agents from Eriodictyon californium.Journal Natural Products. Mar. 1992. vol. 55(3), pp. 357-363.*

Chemical Senses, vol. 19, No. 4 (month unavailable) 1994, pp. 349-358, Claire Johnson, Gordon G. Birch and Douglas B. MacDougall, "The effect of the sweetness inhibitor 2(-4-methoxyphenoxy)propanoic acid (sodium salt) (Na-PMP) on the taste of bitter-sweet stimuli".

Manufacturing Chemist, Jul. 2000, pp. 16-17, "Masking the bitter tas".

Nature, vol. 387, Jun. 5, 1997, p. 563, P.A.S. Breslin, G.K. Beauchamp, "Salt enchances flavour by suppressing bitterness".

Phytochemistry, 51, (month uavailable) 1999, pp. 771-780, Jan F. Stevens, Eckhard Wollenweber, Monika Ivancic, Victor L. Hsu, Scott Sundberg, Max L. Deinzer, Leaf surface flavonoids of Chrysothamnus.

J. Am. Chem. Soc., Dec. 1940, vol. 62, pp. 3285-3291, L.C. Copeland and O.A. Short, "Studies of the Ternary Systems $ZnSo_4$-$H_2SO_4$-$H_2O$ from −5 to 70° and $ZnO$-$SO_3$-$H_2O$ at 25°".

Biochemical Systematics and Ecology, vol. 27, (month unavailable) 1999, pp. 755-757, Major exudate flavonoids of *Dubautia arborea*(*Asteraceae*).

William E. Dick, Jr.: "Structure-Taste Correlations for Flavans and Flavanones Conformationally Equivalent to Phyllodulcin"; J. Agric. Food Chem., vol. 29, 1981, pp. 305-312, XP002236604.

Ubeaud, et al.. "In Vitro Inhibition of Simvastatin Metabolism in Rat and Human Liver by Naringenin," Life Sciences, 65:13, 1403-1412 (1999).

* cited by examiner

USE OF HYDROXYFLAVANONES FOR MASKING BITTER TASTE

FIELD OF THE INVENTION

The invention relates to the use of hydroxyl-substituted 2-phenylchroman-4-ones (termed hydroxyflavanones hereinafter), their salts and stereoisomers and mixtures thereof for masking or reducing bitter and/or metallic taste impression. The invention also relates to nutritional, nutritive or consumable preparations, or oral pharmaceutical preparations, characterized in that these have an active content of the designated hydroxyflavanones, their salts and stereoisomers and mixtures of the same.

BACKGROUND OF THE INVENTION

Foods or drinks frequently contain various bitter substances which, although they are characteristic (for example, caffeine in tea or coffee), they can also greatly decrease the value (for example limonoids in citrus juices, bitter aftertaste of many synthetic sweeteners such as aspartame or saccharin). To lower the natural content of bitter substances, therefore, frequently subsequent treatment is necessary, for example by extraction as in the decaffeination of tea or coffee, or enzymatically, for example treatment of orange juice with a glycosidase to destroy the bitter naringin, or use of special peptidases in the ripening of cheese. This treatment causes stress to the product, produces wastes and also produces, for example, solvent residues and other residues (enzymes) in the products. It is, therefore, desirable to find substances, preferably natural or nature-identical substances, which can effectively suppress, or at least decrease, the bitter taste or aftertaste.

Suppressing the bitter taste in many pharmaceutically active compounds is particularly important, since, as a result, the readiness of the patients, in particular in the case of patients who are sensitive to bitter taste, such as children, to take the preparation orally, can be significantly increased. Many pharmaceutically active compounds, for example quinine, have a pronounced bitter taste and/or aftertaste.

To date, only a few substances have been described which suppress bitterness and have no inherent taste. Thus, U.S. Pat. No. 6,083,459 describes bitter-masking amino acid derivatives which do not, however, occur in nature. 2(-4-Methoxyphenoxy)propionic acid sodium salt (Lactisol) exhibits a weak bitter-reducing effect at relatively high concentrations (450 ppm), as reported in Chem. Senses, 1994, vol. 19, pp. 349 ff.; however, it is a problem that the substance at the same time suppresses the sweet taste impression (U.S. Pat. No. 4,567,053). Neohesperidin dihydrochalcone also exhibits a bitter-reducing effect, but is primarily a sweetener (see Manufacturing Chemist 2000, July issue, pp. 16-17), which also has a disturbing action in non-sweet applications. Although U.S. Pat. No. 5,580,545 describes taste-modifying properties for some flavones (2-phenylchrom-2-en-4-ones), a bitter-reducing or bitter-suppressing action was not found.

Sodium chloride exhibits a bitter-masking effect against many bitter substances (e.g. Nature, 1997, vol. 387, p. 563); however, the intake of relatively large amounts of salt can lead, for example, to cardiovascular disorders.

Concentrated extracts of Herba Santa or simple aqueous or alcoholic extracts of the same exhibit a weak bitter-masking action towards quinine; however, to date the individual constituents have not been analyzed for their activity; in addition, the extracts display a rather strong herb-like inherent taste.

WO 00/21,390 describes polyglutamic acid as a bitterness-suppressing agent; relatively high concentrations in the region of 1% by weight are required. A lipoprotein consisting of β-lactoglobulin and phosphatic acid also exhibits a bitter-masking effect (EP-A 635 218). Such polymers, however, are difficult to characterize and to standardize.

The flavone glycoside Neodiosmin (5,7-dihydroxy-2-(4-methoxy-3-hydroxyphenyl)-7-O-neohesperidosyl-chrom-2-en-4-one) shows a bitter-suppressing action (U.S. Pat. No. 4,154,862), but features a disaccharide radical which makes preparation and applicability of the substance difficult.

SUMMARY OF THE INVENTION

It was an object of the present invention to find readily accessible low molecular weight substances which exhibit a bitter-suppressing effect against a multiplicity of bitter substances.

The invention therefore relates to the use of compounds of the general formula (I)

where
R$^1$ to R$^9$ independently of one another denote hydrogen atoms, hydroxyl groups, methyl, ethyl, 1-propyl, 2-propyl, methoxy, ethoxy, 1-propyloxy or 2-propyloxy groups, with the proviso that at least one of the radicals R$^1$ to R$^9$ represents a hydroxyl group,
as a constituent of nutritional, nutritive or consumable preparations, and also oral pharmaceutical preparations, comprising at least one bitter substance or a substance which causes a bitter aftertaste, for masking or reducing the bitter or metallic taste impression.

DETAILED DESCRIPTION OF THE INVENTION

Bitter substances within the meaning of the invention can be, for example: xanthine alkaloids (for example caffeine, theobromine), quinoline derivatives (for example quinine) limonoids (for example limonine from citrus fruits), polyphenols (for example catechols, flavonols, γ-oryzanol, hesperitin), pharmaceutically active compounds (for example fluoroquinolone antibiotics, aspirin, β-lactam antibiotics, ambroxol, paracetamol, aspirin, guaifenesin), denatonium benzoate, sucralose octaacetate, potassium chloride, magnesium salts, urea, bitter amino acids (for example tryptophan) and bitter peptide fragments (for example having a terminal leucine or isoleucine radical).

Substances which have a bitter aftertaste within the meaning of the invention can be, for example: aspartame, neotame, saccharin and cyclamate.

The nutritional, nutritive or consumable preparations within the meaning of the present invention are, for example, bakery products (for example bread, dried biscuits, cake, other bakery products), confectionery (for example chocolates, hard and soft toffees, chewing gum), alcoholic or non-alcoholic beverages (for example coffee, tea, wine, beer, liqueurs, spirits, wine brandies, fruit-containing lemonades, isotonic drinks, soft drinks, nectars, fruit and vegetable juices, fruit or vegetable juice preparations), instant drinks, meat products (for example ham, sausage preparations), cereal products (for example breakfast cereals, muesli bars), milk products (for example milk drinks, dairy ice-cream, yogurt, kefir, cheese, dried milk powder, whey), fruit preparations (for example jams, fruit ice, fruit sauces), vegetable preparations (for example ketchup, sauces), snack items (for example fried potato crisps, maize- or peanut-based extrudates), oil- and fat-based products or emulsions of the same (for example mayonnaise, remoulade, dressings), seasonings, fragrance, flavoring and taste compositions, spice mixtures, ready-to-eat dishes and soups. The preparations within the meaning of the invention, particularly preferably the fragrance, flavoring and taste compositions and spice mixtures, can also, as semi-manufactured products, serve for producing further preparations serving for nutrition or pleasure.

Oral pharmaceutical preparations within the meaning of the invention are preparations which exist, for example, in the form of capsules, tablets (non-coated and coated tablets, for example coatings resistant to gastric juice), dragees, granules, pellets, solids mixtures, dispersions in liquid phases, as emulsions, as powders, as solutions, as pastes or as other preparations which can be swallowed or chewed, and are used as drugs requiring prescriptions, sale by pharmacist or other drugs, or as food supplements.

Preference is given to the use of compounds of the general formula (I),
where
$R^2$, $R^4$, $R^5$ and $R^9$ represent hydrogen atoms,
$R^1$, $R^3$, $R^6$, $R^7$ and $R^8$ independently of one another denote hydrogen atoms, hydroxyl groups, methyl, methoxy or ethoxy groups, with the proviso that at least one of the radicals $R^6$ to $R^8$ represents a hydroxyl group,
as a constituent of nutritional, nutritive or consumable preparations, and also oral pharmaceutical preparations comprising at least one bitter substance or a substance causing a bitter aftertaste, for masking or reducing the bitter or metallic taste impression.

Preference is given to the use of compounds of the general formula (I), where
$R^2$, $R^4$, $R^5$, $R^8$ and $R^9$ represent hydrogen atoms,
$R^1$, $R^3$ and $R^6$ independently of one another denote hydrogen atoms, hydroxyl or methoxy groups, with the proviso that at least one of the radicals $R^1$ and $R^3$ represents a hydroxyl group, and
$R^7$ represents a hydroxyl group,
in nutritional, nutritive or consumable preparations and also oral pharmaceutical preparations comprising at least one bitter substance or a substance which causes a bitter aftertaste, for masking or reducing the bitter or metallic taste impression.

The inventive hydroxyflavanones can preferably exist as monovalent anions, or, in the case of a plurality of hydroxyl groups, as polyvalent anions, where the counterions are the cations with a single positive charge of the first main group and subgroup of the Periodic Table of the Elements, the ammonium ion, a trialkylammonium ion, the cations with a double charge of the second main group and subgroup of the Periodic Table of the Elements, and the trivalent cations of the 3rd main group and subgroup, preferably $Na^+$, $K^+$, $NH_4^+$, $Ca^{2+}$, $Mg^{2+}$, $Al^{3+}$ and $Zn^{2+}$.

The inventive hydroxyflavanones can exist as (2S)- or (2R)-enantiomers or as a mixture of the two. Preferably, the inventive hydroxyflavanones are present as a (2S)-enantiomer or as a (2S)-enantiomer-enriched mixture.

Without restricting the invention thereto, the following exemplary compounds may be mentioned: 2-(4-hydroxyphenyl)-5,7-dihydroxychroman-4-one (naringenin), 2-(3,4-dihydroxyphenyl)-5,7-dihydroxychroman-4-one (eriodictyol), 2-(3,4-dihydroxyphenyl)-5-hydroxy-7-methoxychroman-4-one (eriodictyol 7-methyl ether), 2-(3,4-dihydroxyphenyl)-7-hydroxy-5-methoxychroman-4-one (eriodictyol 5-methyl ether) and 2-(4-hydroxy-3-methoxyphenyl)-5,7-dihydroxychroman-4-one (homoeriodictyol), their (2S)- or (2R)-enantiomers, or mixtures of the same and their monovalent or polyvalent phenolate salts with $Na^+$, $K^+$, $NH_4^+$, $Ca^{2+}$, $Mg^{2+}$ or $Al^{3+}$ as counterions.

The diagram below illustrates the structures of the inventive examples preferred in particular:

Eriodictyol-5-methyl-ether

The monosodium and disodium salts of (+)-(2S)-homoeriodictyol are preferred.

Obviously, the various inventive hydroxyflavanones, their stereoisomers and salts can be used according to the present invention in each case, alone or as mixtures.

Surprisingly, it has been found that the inventive hydroxyflavanones, even at very low concentrations, can reduce or even completely suppress the bitter taste impression of a multiplicity of bitter substances, in particular of methylxanthines, for example caffeine, alkaloids, for example quinine, flavonoids, for example naringin, inorganic salts, such as potassium chloride or magnesium sulfate, pharmaceutically active compounds, for example β-lactam antibiotics, paracetamol, guaifenesin, in which case it is particularly advantageous that the inventive hydroxyflavanones have virtually no inherent taste. In particular, the inventive hydroxyflavanones are active directly in the preparation on intake into the mouth, and need not be consumed prior to the bitter substance.

Some of the hydroxyflavanones have long been known and have been found in nature; for example naringenin occurs in grapefruits bound as glycoside; homoeriodictyol has been isolated as minor component from Chryothamnus spp. (Phytochemistry, 1999, volume 51, issue 6, pp. 771-780) and has been isolated together with eriodictyol from Eriodictyon californicum (J. Am. Chem. Soc. 1940, volume 62, p. 3285). Eriodictyol 7-methyl ether has been isolated from Dubantia arborea (Biochem. Syst. Ecol., 1999, vol. 27, issue 7, pp. 755-757).

The invention further relates to nutritional, nutritive or consumable preparations or oral pharmaceutical preparations characterized in that they have an active content of hydroxyflavanones, their salts or their mixtures. They generally comprise 0.000001% by weight to 10% by weight, preferably 0.00001% to 1% by weight, but more preferably 0.0001% by weight to 0.1% by weight, based on the total weight of the preparation, of inventive hydroxyflavanones, their salts or their mixtures. Other customary active compounds, base compounds, aids and additives for food consumed for nutrition or pleasure or oral pharmaceutical preparations can be present in amounts of 5 to 99.999999% by weight, preferably 10 to 80% by weight, based on the total weight of the preparation. In addition, the preparations can comprise water in an amount up to 99.999999% by weight, preferably 5 to 80% by weight, based on the total weight of the preparation.

The inventive preparations that serve as semi-manufactured products generally comprise 0.0001% by weight to 95% by weight, preferably 0.1 to 80% by weight, but in particular 1% by weight to 50% by weight, based on the total weight of the preparation, of inventive hydroxyflavanones, their salts or their mixtures.

The inventive preparations comprising one or more of the inventive hydroxyflavanones are produced in such a manner that the inventive hydroxyflavanones are incorporated into the nutritional, nutritive or consumable preparations as the substances themselves, as solution or in the form of a mixture with a solid or liquid carrier.

To produce the preparations, in a further embodiment, the inventive hydroxyflavanones and, if appropriate, other constituents of the inventive preparation can also be incorporated in advance into emulsions, into liposomes, for example based on phosphatidylcholine, into microspheres, into nanospheres or into capsules made of a matrix suitable for foods and drinks, for example made of starch, starch derivatives, other polysaccharides, natural fats, natural waxes or proteins, for example gelatin. A further embodiment is that the inventive hydroxyflavanones are complexed in advance with suitable complexing agents, for example with cyclodextrins or cyclodextrin derivatives, preferably β-cyclodextrin, and are used in this form.

Other constituents which can be used for the inventive nutritional, nutritive or consumable preparations are customary bases, aids, and additives for foods and drinks, for example water, mixtures of fresh or processed, plant or animal, base substances or raw materials (for example raw, roasted/fried, dried, fermented, smoked and/or boiled meat, bones, cartilage, fish, vegetables, fruits, herbs, nuts, vegetable or fruit juices or pastes or their mixtures), digestible or indigestible carbohydrates (for example sucrose, maltose, fructose, glucose, dextrins, amylose, amylopectin, inulin, xylan, cellulose), sugar alcohols (for example sorbitol), natural or hardened fats (for example tallow, lard, palm fat, coconut fat, hardened vegetable fat), oils (for example sunflower oil, peanut oil, corn oil, olive oil, fish oil, soya bean oil, sesame oil), fatty acids or their salts (for example potassium stearate), proteinogenic or non-proteinogenic amino acids and related compounds (for example taurine), peptides, native or processed proteins (for example gelatin), enzymes (for example peptidases), nucleic acids, nucleotides, flavor enhancers (for example sodium glutamate, inositol phosphate, 2-phenoxypropionic acid), emulsifiers (for example lecithins, diacylglycerols, monoacylglycerols), stabilizers (for example caragheenan, alginate), preservatives (for example benzoic acid, sorbic acid), antioxidants (for example tocopherol, ascorbic acid), chelators (for example citric acid), organic or inorganic acidulants (for example malic acid, acetic acid, citric acid, tartaric acid, phosphoric acid), additional bitter substances (for example quinine, caffeine, limonine), sweeteners (for example saccharin, cyclamate, aspartame, neotame), mineral salts (for example sodium chloride, potassium chloride, magnesium chloride, sodium phosphates), the substances inhibiting enzymatic browning (for example sulfur dioxide, sulfite, ascorbic acid), essential oils, plant extracts, natural or synthetic dyes or colored pigments (for example carotenoids, flavonoids, anthocyans, chlorophylls and their derivatives), spices, synthetic, natural or nature identical flavorings or fragrances and odor-correctives and taste-correctives not affecting the bitter taste.

Other constituents which can be used for the inventive oral pharmaceutical preparations are all customary further active compounds, base substances, aids and additives for oral pharmaceutical preparations. Active compounds which can be used are all bitter- or metallic-tasting pharmaceutical compounds which can be formulated for oral preparations. The active compounds, base substances, aids and additives can be converted into the oral dosage forms in a manner known per se. This takes place with the use of inert non-toxic pharmaceutically compatible aids. These include, inter alia, carriers (for example microcrystalline cellulose), solvents (for example liquid polyethylene glycols), emulsifiers (for example sodium dodecyl sulfate), dispersants (for example polyvinylpyrrolidone), synthetic and natural biopolymers (for example albumin), stabilizers (for example antioxidants such as ascorbic acid), colorants (for example inorganic pigments such as iron oxides) or odor-correctives and taste-correctives not affecting the bitter taste.

Preferably, the inventive preparations can also comprise a flavoring composition to round and refine the taste and/or odor of the preparation. Suitable flavoring compositions comprise, for example, synthetic, natural or nature identical flavorings, fragrances and taste substances and suitable aids and carriers. It is considered here to be particularly advantageous that the bitter or metallic taste impression can be suppressed or reduced by flavorings or fragrances present in the inventive flavoring compositions and thus the entire flavor or taste profile can be improved.

The invention further relates to the use of the nutritional, nutritive or consumable preparations, or pharmaceutical preparations, as semi-manufactured products for suppressing or reducing the bitter taste or aftertaste of preparations manufactured therefrom as finished products.

Finished products within the meaning of the invention are ready to use products for end consumers and are, for example, mentioned on page 5 of the specification.

Semi-finished products within the meaning of the invention are preparations, which were mixed or blended with other semi-finished food products or finished products.

EXAMPLES

The examples serve only to illustrate the invention, without restricting it thereto.

Example 1

Debittering Black Tea

Two different types of black tea were brewed using boiling water (3 g of tea to 100 ml, allowed to infuse for 3 min, filter) and were then tasted by an expert group. The bitterness was rated using a scale of 1 to 5 (1 just perceptibly bitter, 5 very bitter). The results are shown in the table below:

TABLE 1

| Sample | Rating (1–5) |
| --- | --- |
| Tea sample 1 | 3.5 |
| Tea sample 2 | 5 |
| Tea sample 2 + 0.05% homoeriodictyol disodium salt | 2 |

Example 2

Masking the Bitter Taste of a β-lactam Antibiotic

A solution of Faropenem Daloxate ([5R-[3(R*),5α,6α (R*)]]-6-(1-hydroxyethyl)-7-oxo-3-(tetrahydro-2-furanyl)-4-thia-1-azabicyclo[3.2.0]hept-2-ene-2-carboxylic acid (5-methyl-2-oxo-1,3-dioxol-4-yl)methyl ester, CAS No. 141702-36-5, 0.1% by weight in water, sample 1) and a mixture of Faropenem Daloxate+homoeriodictyol disodium salt (each 0.1% by weight in water, sample 2) were made up. A group of 7 testers were each given 3 samples for difference testing. 4 testers received sample 1 as a duplicate sample, 3 testers received sample 2 as a duplicate sample. The samples were tasted in differing orders. Of 7 testers, 7 correctly identified the individual sample. The average bitter intensity of sample 1 was rated 5, that of sample 2 was rated 2 (scale 1 to 5).

Example 3

Reducing Bitterness of a Caffeine Solution by (2S)-homoeriodictyol Disodium Salt To quantify the reduction in bitter impression, the bitterness of a 500 ppm-containing caffeine solution and a sample which contained 500 ppm of caffeine and various amounts of (2S)-homoeriodictyol disodium salt was determined.

Figure 1:
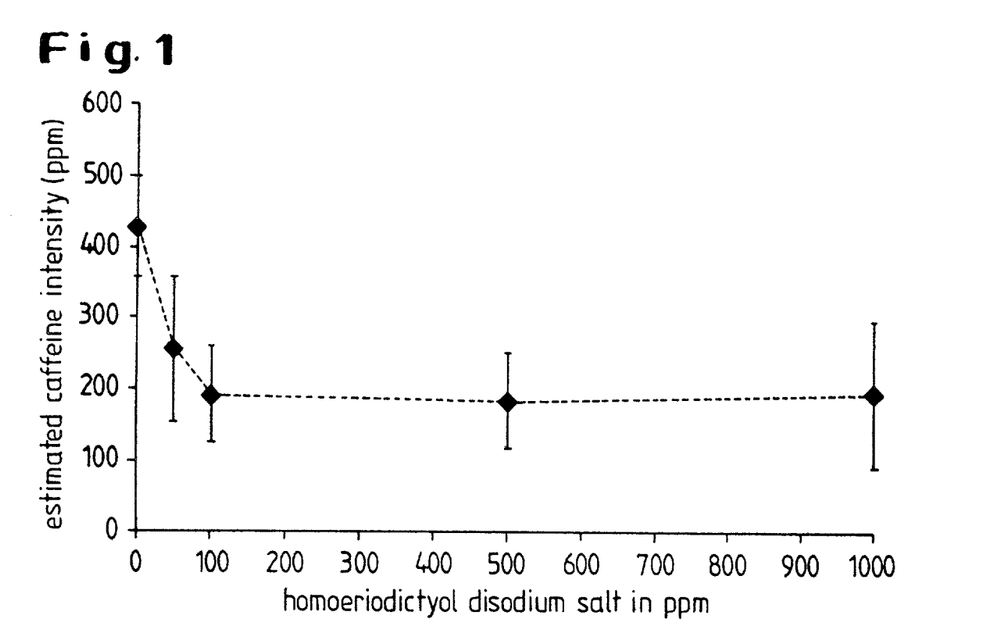
FIG. 1 shows a graph of the course of bitterness intensity of a solution containing 500 ppm of caffeine with increasing concentration of (2S)-homoeriodictyol disodium salt compared with a series of caffeine concentrations (100 to 500 ppm)

To categorize the test samples, a reference series was prepared using 10 different concentrations of caffeine in water (50, 100, 150, 200, 250, 300, 350, 400, 450 and 500 ppm). In the diagram hereinafter, the dependence of recognition of bitterness on the amount of homoeriodictyol disodium salt added may be seen:

FIG. 1 shows the course of bitterness intensity of a solution containing 500 ppm of caffeine with increasing concentration of (2S)-homoeriodictyol disodium salt compared with a series of caffeine concentrations (100 to 500 ppm)

Example 4

Reduction in Bitterness of a Caffeine Solution by Various Hydroxyflavanones

Similarly to Example 3, a caffeine solution (500 ppm) with or without 100 ppm of (2S)-homoeriodictyol, (2S)-homoeriodictyol disodium salt, (2S)-eriodictyol, (2S)-eriodictyol 7-methyl ether and (2S)-naringenin was tasted and classified on the basis of the reference series.

Figure 2:
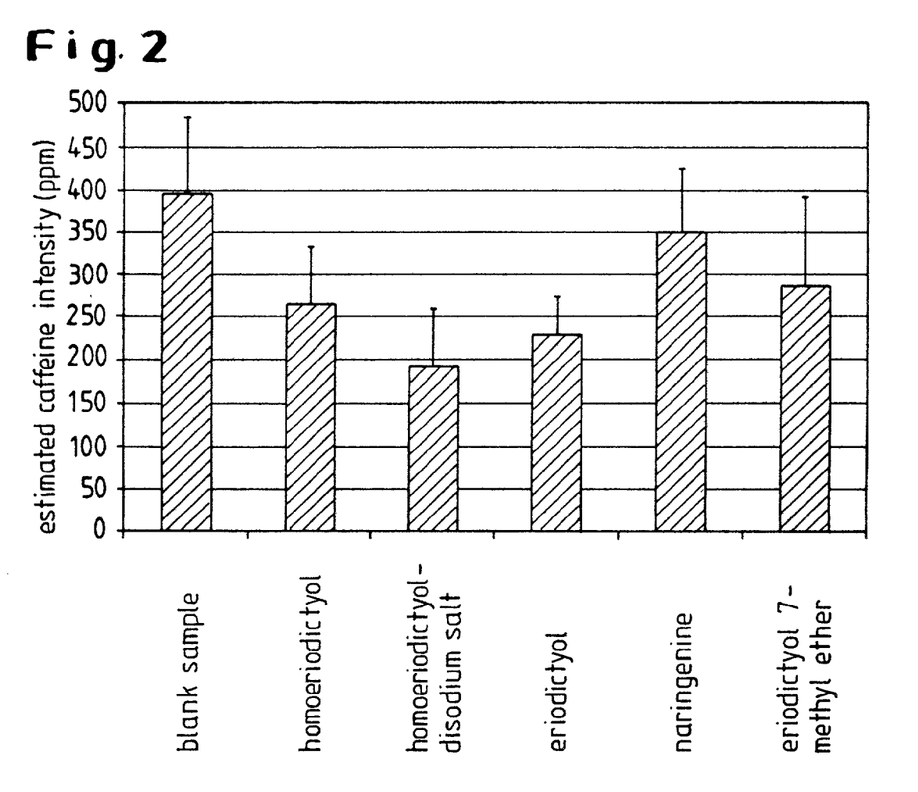
FIG. 2 shows a graph of the estimated caffeine intensity of a solution containing 500 ppm of caffeine and 100 ppm of an exemplary hydroxyflavanone.

FIG. 2 shows the estimated caffeine intensity of a solution containing 500 ppm of caffeine and 100 ppm of an exemplary hydroxyflavanone.

Example 5

The bitter impressions of a paracetamol solution, a paracetamol/homoeriodictyol disodium salt solution and a solution containing paracetamol/homoeriodictyol disodium salt and chocolate flavoring were classified on a scale of 1 to 9.

Figure 3:
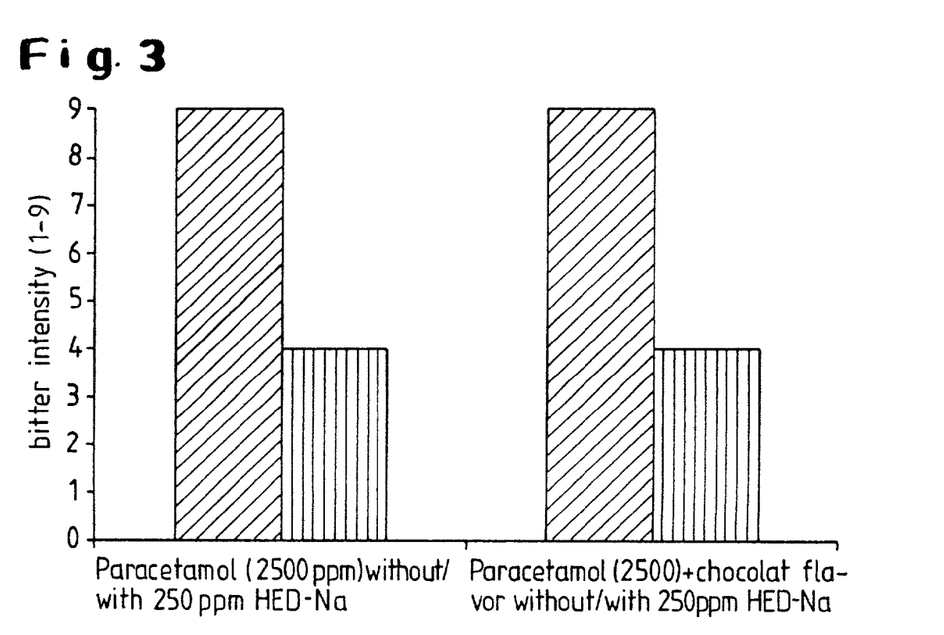
FIG. 3 shows a graph of the decrease in bitter intensity for paracetamol.

FIG. 3 shows the decrease in bitter intensity for paracetamol.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A preparation comprising a bitter substance masking compound for oral ingestion selected from the group consisting of 2-(3,4-dihydroxyphenyl)-5-hydroxy-7-methoxychroman-4-one (eriodictyol 7-methyl ether), 2-(3,4-dihydroxyphenyl)-7-hydroxy-5-methoxychroman-4-one (eriodictyol 5-methyl ether), 2-(4-hydroxy-3-methoxyphenyl)-5,7-dihydroxychroman-4-one (homoeriodictyol), wherein said preparation is a food preparation or a drink preparation, wherein said preparation comprises 0.000001% by weight to 10% by weight, based on the total weight of the preparation, of said bitter substance masking compound, wherein said preparation is a nutritional, nutritive or consumable preparations selected from the group consisting of bakery products, confectionery, alcoholic beverages, non-alcoholic beverages, instant drinks, meat products, cereal products, milk products, snack items, oil- and fat-based products or emulsions of the same, seasonings, fragrance, flavoring and taste compositions, spice mixtures, ready-to-eat dishes and soups.

2. A preparation according to claim 1, wherein said bitter substance masking compound exists as a monovalent anion or, in the case of a plurality of hydroxyl groups, as a polyvalent anion, and counterions are cations with a single positive charge of the first main group and subgroup of the Periodic Table of the Elements, the ammonium ion, a trialkylammonium ion, the cations with a double charge of the second main group and subgroup of the Periodic Table of the Elements, and the trivalent cations of the 3rd main group and subgroup of the Periodic Table of the Elements.

3. A preparation according to claim 1, wherein said bitter substance masking compounds consist of (2S)-enantiomers or a (2S)-enantiomer enriched mixture of said bitter substance masking compounds.

4. A preparation comprising a bitter substance masking compound for oral ingestion selected from the group consisting of 2-(3,4-dihydroxyphenyl)-5-hydroxy-7-methoxychroman-4-one (eriodictyol 7-methyl ether), 2-(3,4-dihydroxyphenyl)-7-hydroxy-5-methoxychroman-4-one (eriodictyol 5-methyl ether) and 2-(4-hydroxy-3-methoxyphenyl)-5,7-dihydroxychroman-4-one (homoeriodictyol); and
a bitter substance, wherein said preparation is an oral pharmaceutical preparation, and comprises 10 ppm to 1% by weight, based on the total weight of the preparation, of said bitter substance masking compounds, wherein said bitter substance is selected from the group consisting of β-lactam antibiotics, ambroxol, paracetamol, aspirin, guaifenesin.

5. A preparation according to claim 1, wherein said preparation is a semi-manufactured product.

6. A preparation according to claim 4, wherein said preparation is a semi-manufactured product.

7. A preparation according to claim 1, wherein said preparation is a flavoring and taste compositions and spice mixtures.

8. A preparation comprising a bitter substance masking compound for oral ingestion selected from the group consisting of 2-(3,4-dihydroxyphenyl)-5-hydroxy-7-methoxychroman-4-one (eriodictyol 7-methyl ether), 2-(3,4-dihydroxyphenyl)-7-hydroxy-5-methoxychroman-4-one (eriodictyol 5-methyl ether) and 2-(4-hydroxy-3-methoxyphenyl)-5,7-dihydroxychroman-4-one (homoeriodictyol), wherein said preparation comprises at least one bitter substance or substance with a bitter aftertaste, wherein said bitter substance masking compound is present in a sufficient amount to mask or reduce the bitterness of said bitter substance, wherein said preparation comprises 0.000001% by weight to 10% by weight, based on the total weight of the preparation, of said bitter substance masking compound wherein said bitter substance is selected from the group consisting of denatonium benzoate, sucralose octaacetate, potassium chloride, magnesium salts, urea, bitter amino acids and bitter peptide fragments, and mixtures thereof, and
wherein said substance with a bitter aftertaste is selected from the group consisting of aspartame, neotame, saccharin, cyclamate, and combinations thereof.

9. A preparation according to claim 1, wherein said preparation comprises at least one further bitter-masking substance.

10. A preparation according to claim 1, comprising an additional flavoring composition.

11. A method for masking a bitter substance, the method comprising:
providing a preparation for oral ingestion that includes a bitter substance,
adding a sufficient amount of bitter substance masking compound of general formula (I) to mask or reduce the bitterness of said preparation, wherein compounds of formula (I) have the following structure wherein in formula (I), $R^2$, $R^4$, $R^5$ and $R^9$ represent hydrogen atoms and $R^1$, $R^3$, $R^6$, $R^7$ and $R^8$ independently of one another denote hydrogen atoms, hydroxyl groups, methyl, methoxy or ethoxy groups, with the proviso that at least one of the radicals $R^6$ to $R^8$ represents a hydroxyl group, wherein said adding step comprises adding 0.000001% by weight to 10% by weight, based on the total weight of the preparation, of said bitter substance masking compound, wherein said preparation is a nutritional, nutritive or consumable preparations selected from the group consisting of bakery products, confectionery, alcoholic beverages, non-alcoholic beverages, instant drinks, meat products, cereal products, milk products, snack items, oil- and fat-based products or emulsions of the same, seasonings, fragrance, flavoring and taste compositions, spice mixtures, ready-to-eat dishes and soups.

12. A method for masking a bitter substance, said method comprising:
providing a preparation for oral ingestion that includes a bitter substance, and
adding a sufficient amount of bitter substance masking compound of general formula (I) to mask or reduce the bitterness of said preparation, wherein compounds of formula (I) have the following structure wherein in formula (I), $R^2$, $R^4$, $R^5$, $R^8$ and $R^9$ represent hydrogen atoms and $R^1$, $R^3$ and $R^6$ independently of one another denote hydrogen atoms, hydroxyl or methoxy groups, with the proviso that $R^3$ represents a hydroxyl group, and $R^7$ represents a hydroxyl group, wherein said adding step comprises 0.000001% by weight to 10% by weight, based on the total weight of the preparation, of said bitter substance masking compound, wherein said preparation is a nutritional, nutritive or consumable preparations selected from the group consisting of bakery products, confectionery, alcoholic beverages, non-alcoholic beverages, instant drinks, meat products, cereal products, milk products, snack items, oil- and fat-based products or emulsions of the same, seasonings, fragrance, flavoring and taste compositions, spice mixtures, ready-to-eat dishes and soups.

13. The preparation according to claim 4, wherein said bitter masking compound comprises homoeriodictyol, a monosodium salt of homoeriodictyol, or a disodium salt of homoeriodictyol.

14. The preparation according to claim 8, wherein said bitter masking compound comprises homoeriodictyol, a monosodium salt of homoeriodictyol, or a disodium salt of homoeriodictyol.

15. The method according to claim 11, wherein said bitter substance masking compound of general formula (I) consists of (2S)-enantiomers or a (2S)-enantiomer enriched mixture of said bitter substance masking compounds.

16. The method of claim 11, wherein said bitter substance masking compound of general formula (I) is selected from the group consisting of 2-(3,4-dihydroxyphenyl)-5-hydroxy-7-methoxychroman-4-one (eriodictyol 7-methyl ether), 2-(3,4-dihydroxyphenyl)-7-hydroxy-5-methoxychroman-4-one (eriodictyol 5-methyl ether), and 2-(4-hydroxy-3-methoxyphenyl)-5,7-dihydroxychroman-4-one (homoeriodictyol).

17. The method according to claim 16, wherein said bitter substance masking compound exists as a monovalent anion or, in the case of a plurality of hydroxyl groups, as a polyvalent anion, and counterions are cations with a single positive charge of the first main group and subgroup of the Periodic Table of the Elements, the ammonium ion, a trialkylammonium ion, the cations with a double charge of the second main group and subgroup of the Periodic Table of the Elements, and the trivalent cations of the 3rd main group and subgroup of the Periodic Table of the Elements.

18. The method of claim 11, wherein said bitter substance masking compound of general formula (I) comprises 2-(4-hydroxy-3-methoxyphenyl)-5,7-dihydroxychroman-4-one (homoeriodictyol), a monosodium salt of homoeriodictyol, or a disodium salt of homoeriodictyol.

19. The preparation according to claim 8, wherein said preparation is a nutritional, nutritive or consumable preparations selected from the group consisting of bread, dried biscuits, cake, other bakery products, chocolates, hard toffees, soft toffees, chewing gum, coffee, tea, wine, beer, liqueurs, spirits, wine brandies, isotonic drinks, soft drinks, instant drinks, ham preparations, sausage preparations, breakfast cereals, muesli bars, milk drinks, dairy ice-cream, yogurt, kefir, cheese, dried milk powder, whey, fried potato crisps, maize- or peanut-based extrudates, mayonnaise, remoulade, dressings, and mixtures thereof.

20. The preparation according to claim 1, wherein said preparation is a nutritional, nutritive or consumable preparations selected from the group consisting of bread, dried biscuits, cake, other bakery products, chocolates, hard toffees, soft toffees, chewing gum, coffee, tea, wine, beer, liqueurs, spirits, wine brandies, isotonic drinks, soft drinks, instant drinks, ham preparations, sausage preparations, breakfast cereals, muesli bars, milk drinks, dairy ice-cream, yogurt, kefir, cheese, dried milk powder, whey, fried potato crisps, maize- or peanut-based extrudates, mayonnaise, remoulade, dressings, and mixtures thereof.

* * * * *